(12) United States Patent
El-Sherbeini et al.

(10) Patent No.: US 6,746,858 B1
(45) Date of Patent: Jun. 8, 2004

(54) **MURD PROTEIN AND GENE OF *STREPTOCOCCUS PYOGENES***

(75) Inventors: Mohammed El-Sherbeini, Rahway, NJ (US); Kenny Kin Wong, Rahway, NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 09/530,838

(22) PCT Filed: Oct. 30, 1998

(86) PCT No.: PCT/US98/23054

§ 371 (c)(1),
(2), (4) Date: May 3, 2000

(87) PCT Pub. No.: WO99/23201

PCT Pub. Date: May 14, 1999

Related U.S. Application Data

(60) Provisional application No. 60/064,205, filed on Nov. 4, 1997.

(51) Int. Cl.$^7$ .......................... C12N 9/00; C12N 15/63; C12N 1/00; C12N 15/52; C12P 21/02
(52) U.S. Cl. ................... 435/183; 435/69.1; 435/320.1; 435/252.3; 435/254.11; 536/23.2
(58) Field of Search ............................. 435/69.1, 320.1, 435/183, 252.3, 254.11; 536/23.2, 24.32

(56) References Cited

U.S. PATENT DOCUMENTS 5,681,694 A * 10/1997 Hoskins et al. ................ 435/4

OTHER PUBLICATIONS

Mengin–Lecreulx, D. et al., "Nucleotide sequence of the murD gene . . . synthetase of *Escherichia coli*" Nucleic Acids Research 18, 1990, p. 183.
Michaud, C. D. Blanot, et al., "Partial Purification and specificity studies of the D–glutamate–adding . . . from *Escherichia coli*" Eur J. Biochem 166, 1987, pp. 631–637.
Michaud, C., et al., "Revised Interpretation of the sequence containing the murE gene . . . synthease of *Escherichia coli*" Biochem J. 269, 1990, pp. 277–280.
Nathenson, S. G., et al. "Enzymatic synthesis of the peptide in bacterial uridine nucleotides: purification and properties of D–Glutamic acid–adding enzyme" J. Biol. Chem. 239, 1964, pp. 1773–1776.
Pratviel–Sosa, F. et al., Over–production, purification and properties of the uridine diphosphate N–acetylmuramoyl–L–alanine:D–glutamate ligase from *Escherichia coli*. Eur J. Biochem 202(3), 1991, pp. 1169–1176.
Fervetti et al. Complete genome Sequence of an MI Strain of *Streptococcus pyogenes*. Proc. Nat. Acad. Sci, USA. 2001 98(8):4658–4663.
Rogers, H.J., et al., "Biosynthesis of peptidoglycan" In Microbial Cell Walls and Membranes, 1980 Chapman & Hall Ltd. London pp. 239–297.

Schleifer, K. H. et al. "Peptidoglycan types of bacterial cell walls and their taxonomic implications", Bacteriol. Review, 1972, 36: 407–477.
Tanner, M.E., et al. "Phosphinate Inhibitors of the D–Glutamic Acid Adding Enzyme of Peptidoglycan Biosynthesis". J. Org Chem 61: 1996, pp. 1756–1760.
Tao, J. S., et al. "Nucleotide Sequence of the murE gene of *Escherichia coli*" Can J Microbiol. 35, 1989, pp. 1051–1054.
Daniel, R.A. et al. "DNA Sequence of the murE–murD Region of *Bacillus subtilis* 168" J. Gen Microbiol. 139, 1993, pp. 361–370.
Eveland, S.S., et al. "Conditionally Lethal *Escherichia coli* . . . Identification of a Ligase Superfamily". Biochemistry 36 1997 pp. 6223–6229.
Flouret, B. et al., "Reverse–phase high–pressure liquid chromatography . . . of bacterial cell wall peptidoglycan" Anal Biochem 114 1981, pp. 59–63.
Henriques, A. O. et al. "A *Bacillus subtilis* morphogene cluster that includes spoVE is homologous to the mra region of *Escherichia coli*" Biochimie 74 1992, pp. 735–748.
Ikeda, M. et al., "Nucleotide sequence involving murD and an open reading frame ORF–Y spacing murF and ftsW in *Eschericia coli*." Nucleic Acids Res. 18, 1990, p. 1058.
Ikeda, M., et al, "Homology among MurC, MurD, MurE and MurF proteins in *Eschrichia coli* and that between E. coli murG and a possible murG protein in *Bacillus subtilis*." J Gen Appl Microbiol. 36, 1990, pp. 179–187.
Ito, E. et al. Enzymatic synthesis of the peptide in bacterial uridine nucleotides . . . and L–lysine. J Biol Chem 237, 1962, pp. 2689–2695.
Ito, E. et al. "Enzymatic synthesis of the peptide in bacterial uridine nucleotides: Comparative biochemistry", J Biol Chem 248, 1973, pp. 3131–336.
Jin, H., et al., "Structural studies of *Escherichia coli* UDP–N–acetylmuramate: L–alanine ligase" Biochemistry 35, 1996, pp. 14423–14431.
Lugtenberg, E. J. J. , "Studies on *Eschrichia coli* enyzmes involved in the synthesis of Uridine Diphosphate–NAcetyl–Muramyl–pentapeptide" J. Bacteriol. 110, 1972, pp. 26–34.
Mengin–Lecreulx, D. et al. "Cytoplasmic steps of peptidoglycan synthesis in *Escherichia coli*." J Bacteriol. 151, 1982, pp. 1109–1117.
Mengin–Lecreulx, D. et al. "Incorporation of LL–diaminopimelic acid . . . encoded by dapF" J. Bacteriol. 170, 1988, pp. 2031–2039.

(List continued on next page.)

*Primary Examiner*—Gabriele Bugaisky
(74) *Attorney, Agent, or Firm*—Michael D. Yablonsky; Jack L. Tribble

(57) ABSTRACT

This invention provides the murD gene of *Streptococcus pyogenes*. Purified and isolated MurD recombinant proteins are also provided. Nucleic acid sequences which encode functionally active MurD proteins are described. Assays for the identification of modulators of the expression of murD and inhibitors of the activity of MurD, are also provided.

6 Claims, 5 Drawing Sheets

OTHER PUBLICATIONS

Mengin–Lecreulx, D., et al. "Organization of the murE–murG region . . . D–glutamic–acid–adding enzyme" J. Bacteriol. 171, 1989, pp. 6126–6134.

Altschul, S.F. et al., "Basic Local Alignment Search Tool", J Mol Bio. 215, 1990, pp. 403–410.

Blanot, D., et al., "Synthesis of Analogues of Precursors of Bacterial Peptidoglycan". In Peptides, 1983, pp. 311–314.

Parquet, C. et al. "Nucleotide sequences of the murF gene encoding the UDP–MurNAc–pentapeptide synthesase of *Escherichia coli*," Nucleic Acid Res. 17, 1989, p. 53.

* cited by examiner

```
          10                  30                  50
ATGAAAGTGATAAGTAATTTTCAAAACAAAAAAATATTAATATTGGGGTTAGCCAAATCG
MetLysValIleSerAsnPheGlnAsnLysLysIleLeuIleLeuGlyLeuAlaLysSer 70                  90                 110
GGCGAAGCAGCAGCAAAATTATTGACTAAACTTGGTGCTTTAGTGACTGTTAATGATAGT
GlyGluAlaAlaAlaLysLeuLeuThrLysLeuGlyAlaLeuValThrValAsnAspSer 130                 150                 170
AAACCATTTGACCAAAATCCAGCGGCACAAGCCTTGTTGGAAGAGGGGATTAAGGTCATT
LysProPheAspGlnAsnProAlaAlaGlnAlaLeuLeuGluGluGlyIleLysValIle 190                 210                 230
TGTGGTAGCCACCCAGTAGAATTATTAGATGAGGACTTTGAGTACATGGTTAAAAACCCT
CysGlySerHisProValGluLeuLeuAspGluAspPheGluTyrMetValLysAsnPro 250                 270                 290
GGGATTCCTTATGATAATCCTATGGTTAAACGCGCCCTTGCAAAGGAAATTCCCATCTTG
GlyIleProTyrAspAsnProMetValLysArgAlaLeuAlaLysGluIleProIleLeu 310                 330                 350
ACTGAAGTAGAATTGGCTTATTTCGTATCTGAAGCGCCTATTATCGGGATTACAGGATCA
ThrGluValGluLeuAlaTyrPheValSerGluAlaProIleIleGlyIleThrGlySer 370                 390                 410
AACGGGAAGACAACCACAACGACAATGATTGCCGATGTTTTGAATGCTGGCGGGCAATCT
AsnGlyLysThrThrThrThrThrMetIleAlaAspValLeuAsnAlaGlyGlyGlnSer 430                 450                 470
GCACTCTTATCTGGAAACATTGGTTATCCTGCTTCAAAAGTTGTTCAAAAAGCAATTGCT
AlaLeuLeuSerGlyAsnIleGlyTyrProAlaSerLysValValGlnLysAlaIleAla 490                 510                 530
GGTGATACTTTGGTGATGGAATTGTCCTCTTTTCAATTAGTGGGAGTGAATGCTTTTCGC
GlyAspThrLeuValMetGluLeuSerSerPheGlnLeuValGlyValAsnAlaPheArg 550                 570                 590
CCTCATATTGCTGTCATCACTAATTTAATGCCGACTCATCTGGACTATCATGGCAGTTTT
ProHisIleAlaValIleThrAsnLeuMetProThrHisLeuAspTyrHisGlySerPhe 610                 630                 650
GAGGATTATGTTGCTGCTAAATGGATGATTCAAGCTCAGATGACAGAATCAGACTACCTT
GluAspTyrValAlaAlaLysTrpMetIleGlnAlaGlnMetThrGluSerAspTyrLeu 670                 690                 710
ATTTTAAATGCTAATCAAGAGATTTCAGCAACTCTAGCTAAGACCACCCAAGCAACAGTG
IleLeuAsnAlaAsnGlnGluIleSerAlaThrLeuAlaLysThrThrGlnAlaThrVal 730                 750                 770
ATTCCTTTTTCAACTCAAAAAGTGGTTGATGGAGCTTATCTGAAGGATGGAATACTCTAT
IleProPheSerThrGlnLysValValAspGlyAlaTyrLeuLysAspGlyIleLeuTyr
```

FIG.1A

```
                790                    810                   830
TTTAAAGAACAAGCGATTATAGCTGCAACTGACTTAGGTGTCCCAGGTAGCCACAACATT
PheLysGluGlnAlaIleIleAlaAlaThrAspLeuGlyValProGlySerHisAsnIle 850                    870                   890
GAAAATGCCCTAGCAACTATTGCAGTTGCCAAGTTATCTGGTATTGCTGATGATATTATT
GluAsnAlaLeuAlaThrIleAlaValAlaLysLeuSerGlyIleAlaAspAspIleIle 910                    930                   950
GCCCAGTGCCTTTCACATTTTGGAGGCGTTAAACATCGTTTGCAACGGGTTGGTCAAATC
AlaGlnCysLeuSerHisPheGlyGlyValLysHisArgLeuGlnArgValGlyGlnIle 970                    990                  1010
AAAGATATTACCTTCTACAATGACAGTAAGTCAACCAATATTTTAGCCACTCAAAAAGCT
LysAspIleThrPheTyrAsnAspSerLysSerThrAsnIleLeuAlaThrGlnLysAla 1030                   1050                  1070
TTATCAGGTTTTGATAACAGTCGCTTGATTTTGATTGCTGGCGGTCTAGATCGTGGCAAT
LeuSerGlyPheAspAsnSerArgLeuIleLeuIleAlaGlyGlyLeuAspArgGlyAsn 1090                   1110                  1130
GAATTTGACGATTTGGTGCCAGACCTTTTAGGACTTAAGCAGATGATTATTTTAGGAGAA
GluPheAspAspLeuValProAspLeuLeuGlyLeuLysGlnMetIleIleLeuGlyGlu 1150                   1170                  1190
TCCGCAGAGCGTATGAAGCGAGCTGCTAACAAAGCAGAGGTCTCTTATCTTGAAGCTAGA
SerAlaGluArgMetLysArgAlaAlaAsnLysAlaGluValSerTyrLeuGluAlaArg 1210                   1230                  1250
AATGTGGCAGAAGCAACAGAGCTTGCTTTTAAGCTGGCCCAAACAGGCGATACTATCTTG
AsnValAlaGluAlaThrGluLeuAlaPheLysLeuAlaGlnThrGlyAspThrIleLeu 1270                   1290                  1310
CTTAGCCCAGCTAATGCTAGCTGGGATATGTATCCTAATTTTGAGGTTCGTGGGGATGAA
LeuSerProAlaAsnAlaSerTrpAspMetTyrProAsnPheGluValArgGlyAspGlu 1330                   1350
TTTTTGGCAACCTTTGATTGTTTAAGAGGAGATGCC
PheLeuAlaThrPheAspCysLeuArgGlyAspAla
```

```
Eco}  ---MADYQGKNVVIIGLGLTGLSCVDFFLARGVTPRVMDTR----MTPPGL      44
Hin}  ---MNAYQNKNITIIGLGKTGLSCVDYLLSQQANIRVLDTR----KNPTGI      44
Bsu}  VENDQFLQKQHFLILGLAKSGYAASILHEKGLYVAVNDQKPFEENEPAAQ        50
Spy}  MKVISNFQNKKILILGLAKSGEAAAKLLTKLGALVTVNDSKPFDQNPAAQ        50
Sau}  MLNYTGLENKNVLVVGLAKSGYEAAKLLSKLGANVTVNDGKDLSQDAHAK        50

Eco}  DKLPEAVERHTGSLNDEWLMAA--DLIVASPGIALAHPSLSAAADAGIEI        92
Hin}  DKLPQNIPLHTGSLNQEWLLES--DMIVISPGLAVKTPEIQTALKAGVEV        92
Bsu}  KLSEKGIEVVCGEHPVSLFDQHQITILIKNPGIPYENIMVQEAEKKRGIPV       100
Spy}  ALLEEGIKVICGSHPVELLDENF--EYMVKNPGIPYDNPMVKRALAKEIPI        99
Sau}  DLESMGISVVSGSHPLTLLDNN--PIIVKNPGIPYTVSIIDEAVKRGLKL        98

Eco}  VGDIELFCREAQAPIVAITGSNGKSTVTTLVGEMAKAAGVNVGVGGNIGL       142
Hin}  IGDIELFCRAATKPIVGITGSNGKSTVTTLVYEMAKAAGVKVGMGGNIGI       142
Bsu}  WTEIELAYYLTSAKFIGITGSNGKTTTTMIADVLNAGGQSALLSGNIGY       150
Spy}  LTEVELAYFVSEAPIIGITGSNGKTTTTMPTHLDYH-G                149
Sau}  LTEVELSYLISEAPIIAVTGTNGKTTVTSLIGDMFKKSRLTGRLSGNIGY       148

Eco}  PALMLLDDE--CELYVLELSSFQLETTSSLQAVAATLLNVTEDHMDRYPF       190
Hin}  PALSLLNED--CELYVLELSSFQLETTYSLKAAATVLNVTEDHMDRY-M       189
Bsu}  VASEVAYHADGDEWIVTELSSFQLMGTHAFRPEISLILNVFDAHLDYH-H       199
Spy}  PASKVVQKAIAGDTLVGVNAFRPHIAVIINLMPTIHLDYH-G             198
Sau}  VASKVAQEVKPTDYLVTELSSFQLLGIEKYKPHIALITNIYSAHLDYH-E       197

Eco}  GLQQYRAAKLRIYEN---AKVCVVNADDALTMPIR-GADERCVSFGVNMG       236
Hin}  DLEDYRQAKLRLYHN---AKVGVLNNEDRLTFGENENQAKHTVSFAENSA       236
Bsu}  TRENYEKAKQKVYLHQTASDKAIVNQDDETVVRLAEAGKAEIVPFSVSKT       249
Spy}  SFEDYVAAKWMIQAQMTESDYLILNANQEISATLAKTTKATVIPFSTQKV       248
Sau}  NLENYQNAKKQIYKNQTEEDYLICNYHQRQVIE-SEELKAKTLYFSTQQE       246
```

FIG. 2B

```
Eco} DYHLNHQQGETWLRVKGEKVLNVKEMKLSGQHNYTNALAALALADAAGLP  286
Hin} DYWLKTENGKQYLMVKDEVILPCEEATLVGRHNYMNILAATALAQAIGIN  286
Bsu} LEQG--AYVKDSMIMFNGEAILPLEEVVLPGAHNLENIIENALAVVKTAGAS  298
Spy} VDG---AYLKDGILYFKEQAIIATDLGVPGSHNIENALATIAVAKLSGIA  296
Sau} VDG---IYIKDGFIVYKGVRIINTEDLVLPGEHNLENILAAVLACILAGVP  294

Eco} RASSLKALTTFTGLPHRFEVVLEHNGVRWINDSKATNVGSTEAALNGLHV  336
Hin} LDSIRTALRHFKGLDHRFQLVHQANGIRWINDSKATNVGSTVAALAGLYI  336
Bsu} NEAVKKVLTSFFTGVKHRLQYVTTVNGRKFYNDSKATNILATSKALSAFD-  347
Spy} DDIIAQCLSHFGGVKHRLQRVGQIKDITFYNDSKSISTNILATQKALSGFDN  346
Sau} IKALIIDSLTTFSGIEHRLQYVGTNRTNKYYNDSKATNTLATQFALNSFN-  343

Eco} DGTLHLLLGGDGKSADFSPLARYLNGDNVRLYCFGRDGAQLALRPEV---  384
Hin} EGKLHLLLGGDGKGADFISELAELINQPHIICYCFGRDGALLAKFSSQ---  383
Bsu} -KPVILLLTAGGLDRGNGFLLKPYMKH-VKAVLTFGQTAPKLIEKLGNELGI  395
Spy} -SRLILITAGGLDRGNGFLDDLVPDLLG-LKQMIILGESAERMKRAANKAEV  394
Sau} -QPIIWLCGGLDRGNEFDELIIPYMEN-VRAMVVFGQTKAKFAKLGNSQGK  391

Eco} --AEQTETMEQAMRLLAPRVQPGDMVLLSPACASLDQFKNFEQRGNEFAR  432
Hin} --SYLFDTMEQAIIEFLRPTLQSGDMVLLSPACASLDQFASFEKRGEEFTH  431
Bsu} QHVKRVDNVEQAVSAAFALSNEGDVILLSPACASWDQFKTFEERGDMFID  445
Spy} S-YLEARNVAEATELAFKLAQTGDTILLSPANASWDMYPNFEVRGDEFLA  443
Sau} S-VIEANNVEDAVDKVQDIIEPNDVLLSPACASWDQYSTFEERGEKFIE  440

Eco} LAKELLG------  438
Hin} LAQCLT-------  437
Bsu} AVHMLK-------  451
Spy} TFDCLRGDA    452
Sau} RFRAHLPSY    449
```

| | Region I | Region II | Region IV |
|---|---|---|---|
| Spy | GSNGKTT | VMELSSFQL..N...HLDYH..AK | G.HN..N..AT.A..G..HRLQ |

FIG.3

MURD PROTEIN AND GENE OF *STREPTOCOCCUS PYOGENES*

CROSS-REFERENCE TO RELATED APPLICATIONS

This application claims the benefit of U.S. Provisional Application No. 60/064,205, filed Nov. 4, 1997, the contents of which are incorporated herein by reference in their entirety.

STATEMENT REGARDING FEDERALLY-SPONSORED R&D

Not applicable.

REFERENCE TO MICROFICHE APPENDIX

Not applicable.

1. Field of the Invention

This invention relates to the genes and enzymes involved in cell wall synthesis in bacteria, and particularly to the inhibition of such enzymes.

2. Background of the Invention

The molecular target of many naturally-occurring antibiotics, including fosfomycin, cycloserine and b-lactams, is the synthesis of the bacterial cell wall. The frequency with which these types of antibiotics arose in evolution indicates that the pathway of cell wall biosynthesis is a particularly effective point of attack against bacteria. Genetic studies confirm the soundness of this process as a target, as temperature-sensitive alleles of the intracellular pathway genes are lytic, and therefore lethal. Since the building blocks of the cell wall are highly conserved structures in both Gram-positive and Gram-negative bacteria, but are unique to the eubacteria, novel inhibitors of cell wall formation are expected to be both broad spectrum and safe antibiotics.

The bacterial cell wall is a polymer—a single molecule composed of peptidoglycan—that defines the boundary and shape of the cell. Assembled by crosslinking glycan chains with short peptide bridges (Rogers, H. J., H. R. Perkins, and J. B. Ward, 1980, Biosynthesis of peptidoglycan. p. 239–297. In Microbial cell walls and membranes. Chapman & Hall Ltd. London), the completed structure is strong enough to maintain cell integrity against an osmotic pressure differential of over four atmospheres, but also flexible enough to allow the cell to move, grow and divide.

The construction of the peptidoglycan begins in the cytoplasm with an activated sugar molecule, UDP-N-acetylglucosamine. After two reactions (catalyzed by MurA and MurB) that result in the placement of a lactyl group on the 3-OH of the glucosamine moiety, a series of ATP-dependent amino acid ligases (MurC, -D, -E, and -F) catalyze the stepwise synthesis of the pentapeptide sidechain using the newly synthesized lactyl carboxylate as the first acceptor site. After attachment of the sugar pentapeptide to a lipid carrier in the plasma membrane, another glucosamine unit is added to the 4-OH of the muramic acid moiety. The completed monomeric building block is moved across the membrane into the periplasm where the penicillin-binding proteins enzymatically add it into the growing cell wall.

Because the pentapeptide sidechain is not synthesized ribosomally it contains more diverse chemical functionality than a typical peptide, both structurally and stereochemically. Two of the enzymes catalyze the addition of D-amino acids (MurD and MurF) and MurE mediates the formation of a peptide bond between the g-carboxylate of D-glutamate and the amino group of L-lysine. Presumably these structures render the exposed peptidoglycan resistant to the action of proteases, but they also imply that the active sites of the enzymes must have unusual structures in order to handle the somewhat uncommon substrates. These unusual active sites are targets to bind novel inhibitors that can have antimicrobial activity.

Among these potential enzyme targets is MurD. The first partial purification and characterization of a D-glutamate-adding enzyme was from *Staphlococcus aureus* (Ito, E. and J. L. Strominger, 1962, Enzymatic synthesis of the peptide in bacterial uridine nucleotides: Enzymatic addition of L-alanine, D-glutamic acid, and L-lysine. J. Biol. Chem. 237: 2689–2695; Nathenson, S. G., J. L. Strominger, and E. Ito, 1964, Enzymatic synthesis of the peptide in bacterial uridine nucleotides: purification and properties of D-Glutamic acid-adding enzyme, J. Biol. Chem. 239: 1773–177), followed by studies in more detail on the isolated *E. coli* enzyme (Blanot, D., A. Kretsovali, M. Abo-Ghalia, D. Mengin-Lecreulx, and J. van Heijenoort, 1983. Synthesis of analogues of precursors of bacterial peptidoglycan. p. 311–314. In Peptides. Blaha, K. and P. Malon, eds. pp. 311–314, Walter de Gryter and Co. Berlin, N.Y.; Jin, H., Emanuele, J. J., Jr., Fairman, R., Robertson, J. G., Hail, M. E., Ho, H.-T., Falk, P. and Villafranca, J. J., 1996. Structural studies of *Escherichia coli* UDP-N-acetylmuramate:L-alanine ligase. Biochemistry 35: 14423–14431; Ito E. and J. L. Strominger, 1973. Enzymatic synthesis of the peptide in bacterial uridine nucleotides: Comparative biochemistry. J. Biol. Chem. 248: 3131–3136; Michaud, C. D. Blanot, B. Flouret, and J. van Heijenoort, 1987. Partial purification and specificity studies of the D-glutamate-adding and D-alanyl-D-alanine-adding enzymes from *Escherichia coli* K12. Eur. J. Biochem. 166: 631–637). Recently, a purified recombinant *E. coli* MurD was reported (Pratviel-Sosa F, D. Mengin-Lecreulx and J. van Heijenoort, 1991. Overproduction, purification and properties of the uridine diphosphate N-acetylmuramoyl-L-alanine:D-glutamate ligase from *Escherichia coli*. Eur. J. Biochem. 202 (3):1169–1176) and genes encoding MurD have been cloned from several species of bacteria including *E. coli* (Ikeda, M., M. Wachi, F. Ishino, and M. Matsuhashi, 1990, Nucleotide sequence involving murD and an open reading frame ORF-Y spacing murF and ftsW in *Escherichia coli*. Nucleic Acids Res. 18:1058; Mengin-Lecreulx, D., C Parquet, L. Desviat, J. Pla, B. Flouret, J. Ayala and J. van Heijenoort, 1989, Organization of the murE-murG region of *Escherichia coli*: Identification of the murD gene encoding the D-glutamic-acid-adding enzyme. J. Bacteriol. 171: 6126–6134) and *B. subtilis* (Daniel, R. A., and J. Errington, 1993, DNA sequence of the murE-murD region of *Bacillus subtilis* 168. J. Gen. Microbiol. 139:361–370; Henriques, A. O. de Lencaster, H. and P. J. Piggot, 1992, A *Bacillus subtilis* morphogene cluster that includes spoVE is homologous to the mra region of *Escherichia coli*. Biochimie. 74: 735–748). Compounds have been designed and synthesized that have inhibitory activity against the *E. coli* enzyme (Tanner, M. E., S. Vaganay, van Heijenoort, J., and D. Blanot, 1996, Phosphinate Inhibitors of the D-Glutamic Acid-Adding Enzyme of Peptidoglycan Biosynthesis. J. Org. Chem. 61: 1756–1760), although they do not have antibacterial activity.

SUMMARY OF THE INVENTION

Polynucleotides and polypeptides of *Streptococcus pyogenes* MurD, an enzyme involved in bacterial cell wall biosynthesis are provided. The recombinant MurD enzyme is catalytically active in ATP-dependent D-glutamate addition reactions. The enzyme is used in in vitro assays to screen for antibacterial compounds that target cell wall biosynthesis. The invention includes the purified polynucleotides, purified enzymes encoded by the polynucleotides, and host cells expressing the recombinant enzyme and their use in assays.

BRIEF DESCRIPTION OF THE DRAWINGS

FIGS. 1A & 1B. Nucleotide sequence and the predicted amino acid sequence of S. pyogenes murD. The amino acid sequence (SEQ ID NO:2) is presented in three-letter code below the nucleotide sequence (nucleotides 18 to 1367 of SEQ ID NO: 1).

FIGS. 2A & 2B. Alignment of the deduced amino acid sequence of S. pyogenes MurD with MurD homologs of E. coli (Eco) (SEQ ID NO:3), H. influenzae (Hin) (SEQ ID NO:4), B. subtilis (Bsu) (SEQ ID NO:5)and S. aureus (Sau) (SEQ ID NO:6). Single letters amino acids are used. Identical residues are indicated by boxes. Gaps are indicated by dashes.

FIG. 3. The murein consensus sequence of the MurD of S. pyogenes (Spy). The murein consensus sequence (shown in bold) was generated by multiple alignments of murein genes murC, -D, -E, and -F from various bacterial genera (Eveland, S. S., D. L. Pompliano, and M. S. Anderson, 1997, Conditionally lethal Escherichia coli murein mutants contain point defects that map to regions conserved among murein and folyl poly-g-glutamate ligases: Identification of a ligase superfamily. Biochemistry. 36: 6223–6229).

DETAILED DESCRIPTION OF THE INVENTION

This invention provides polynucleotides and polypeptides of a cell wall biosynthesis gene from Streptococcus pyogenes, referred to herein as MurD. The polynucleotides and polypeptides are used to further provide expression vectors, host cells comprising the vectors, probes and primers, antibodies against the MurD protein and polypeptides thereof, assays for the presence or expression of MurD and assays for the identification of modulators and inhibitors of MurD.

Bacterial UDP-N-acetylmuramyl-L-alanine:D-glutamate ligase (MurD), a cytoplasmic peptidoglycan biosynthetic enzyme, catalyzes the ATP-dependent addition of D-glutamate to an alanyl residue of the UDP-N-acetylmuramyl-L-alanine precursor, generating the dipeptide.

The murD gene was cloned from Streptococcus pyogenes. Sequence analysis of the S. pyogenes murD gene revealed an open reading frame of 452 amino acids. The deduced amino acid sequence of S. pyogenes MurD is highly homologous to MurD from Escherichia coli, Haemophilus influenzae, Bacillus subtilis and S. aureus (FIGS. 2A & 2B) Recombinant MurD protein from S. pyogenes was over-produced as His-tagged fusion protein in Escherichia coli host cells. The S. pyogenes MurD enzyme was purified to apparent homogeneity. The recombinant enzyme catalyzed the ATP-dependent addition of D-glutamate to the precursor sugar peptide.

As used herein an "inhibitor" is a compound or molecule that interacts with and inhibits or prevents a polypeptide of MurD from catalyzing the ATP-dependent addition of D-glutamate to an alanyl residue of the UDP-N-acetylmuramyl-L-alanine precursor.

As used herein a "modulator" is a compound or molecule that interacts with an aspect of cellular biochemistry to effect an increase or decrease in the amount of a polypeptide of MurD present at the surface of a cell, or in the surrounding serum or media. The change in amount of the MurD polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the receptor or by interacting with another component(s) of cellular biochemistry which directly or indirectly effects the change.

Nucleic acids encoding murD from Streptococcus pyogenes are useful in the expression and production of the S. pyogenes MurD protein. The nucleic acids are also useful in providing probes for detecting the presence of S. pyogenes.

Polynucleotides

A preferred aspect of the present invention is disclosed in FIGS. 1A & 1B and SEQ ID NO:1, an isolated murD polynucleotide encoding a MurD protein from Streptococcus pyogenes, disclosed as follows:

```
GGATAGTGTG  AGCTTAG

ATGAAAGTGA  TAAGTAATTT  TCAAAACAAA  AAAATATTAA  TATTGGGGTT

AGCCAAATCG  GGCGAAGCAG  CAGCAAAATT  ATTGACCAAA  CTTGGTGCTT

TAGTGACTGT  TAATGATAGT  AAACCATTTG  ACCAAAATCC  AGCGGCACAA

GCCTTGTTGG  AAGAGGGGAT  TAAGGTCATT  TGTGGTAGCC  ACCCAGTAGA

ATTATTAGAT  GAGGACTTTG  AGTACATGGT  TAAAAACCCT  GGGATTCCTT

ATGATAATCC  TATGGTTAAA  CGCGCCCTTG  CAAAGGAAAT  TCCCATCTTG

ACTGAAGTAG  AATTGGCTTA  TTTCGTATCT  GAAGCGCCTA  TTATCGGGAT

TACAGGATCA  AACGGGAAGA  CAACCACAAC  GACAATGATT  GCCGATGTTT

TGAATGCTGG  CGGGCAATCT  GCACTCTTAT  CTGGAAACAT  TGGTTATCCT

GCTTCAAAAG  TTGTTCAAAA  AGCAATTGCT  GGTGATACTT  TGGTGATGGA
```

-continued

```
ATTGTCCTCT  TTTCAATTAG  TGGGAGTGAA  TGCTTTTCGC  CCTCATATTG

CTGTCATCAC  TAATTTAATG  CCGACTCATC  TGGACTATCA  TGGCAGTTTT

GAGGATTATG  TTGCTGCTAA  ATGGATGATT  CAAGCTCAGA  TGACAGAATC

AGACTACCTT  ATTTTAAATG  CTAATCAAGA  GATTTCAGCA  ACTCTAGCTA

AGACCACCCA  AGCAACAGTG  ATTCCTTTTT  CAACTCAAAA  AGTGGTTGAT

GGAGCTTATC  TGAAGGATGG  AATACTCTAT  TTTAAAGAAC  AGGCGATTAT

AGCTGCAACT  GACTTAGGTG  TCCCAGGTAG  CCACAACATT  GAAAATGCCC

TAGCAACTAT  TGCAGTTGCC  AAGTTATCTG  GTATTGCTGA  TGATATTATT

GCCCAGTGCC  TTTCACATTT  TGGAGGCGTT  AAACATCGTT  TGCAACGGGT

TGGTCAAATC  AAAGATATTA  CCTTCTACAA  TGACAGTAAG  TCAACCAATA

TTTTAGCCAC  TCAAAAAGCT  TTATCAGGTT  TTGATAACAG  TCGCTTGATT

TTGATTGCTG  GCGGTCTAGA  TCGTGGCAAT  GAATTTGACG  ATTTGGTGCC

AGACCTTTTA  GGACTTAAGC  AGATGATTAT  TTTGGGAGAA  TCCGCAGAGC

GTATGAAGCG  AGCTGCTAAC  AAAGCAGAGG  TCTCTTATCT  TGAAGCTAGA

AATGTGGCAG  AAGCAACAGA  GCTTGCTTTT  AAGCTGGCCC  AAACAGGCGA

TACTATCTTG  CTTAGCCCAG  CTAATGCTAG  CTGGGATATG  TATCCTAATT

TTGAGGTTCG  TGGGGATGAA  TTTTTGGCAA  CCTTTGATTG  TTTAAGAGGA

GATGCCTAAT  GCCTAAGAAG  ATTTTATTTA  CAGGTGGTGG
```

The isolated nucleic acid molecule of the present invention can include a deoxyribonucleic acid molecule (DNA), which can be single (coding or noncoding strand) or double stranded, as well as synthetic DNA, such as a synthesized, single stranded polynucleotide. The isolated nucleic acid molecule of the present invention can also include a ribonucleic acid molecule (RNA).

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the vector can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the MurD gene sequences disclosed herein. Polynucleotides of this invention can be single or double stranded. If single stranded, the polynucleotides can be a coding, "sense," strand or a complementary, "antisense," strand. Antisense strands can be useful as modulators of the gene by interacting with RNA encoding the MurD protein. Antisense strands are preferably less than full length strands having sequences unique or highly specific for RNA encoding the protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methyl-cytosine, deazaguanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxytethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotides, proteins and polypeptides, or respective fragments thereof in question has been removed from its in vivo environment so that it can be manipulated by the skilled artisan, such as but not limited to sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein can be present in whole cells or in cell lysates or in a partially purified or substantially purified form. A polynucleotide is considered purified when it is purified away from environmental contaminants. Thus, a polynucleotide isolated from cells is considered to be substantially purified when purified from cellular components by standard methods while a chemically synthesized nucleic acid sequence is considered to be substantially purified when purified from its chemical precursors.

Polypeptides

The present invention also relates to a substantially purified form of the MurD protein from *Streptococcus pyogenes*, which is shown in FIGS. 1A & 1B and as set forth in SEQ ID NO:2, disclosed as follows:

vide for proteins or protein fragments of diagnostic, therapeutic or prophylactic use and would be useful for screening for modulators, and/or inhibitors of MurD function.

Using the disclosure of polynucleotide and polypeptide sequences provided herein to isolate polynucleotides encoding naturally occurring forms of MurD, one of skill in the art can determine whether such naturally occurring forms are mutant or polymorphic forms of MurD by sequence comparison. One can further determine whether the encoded protein, or fragments of any MurD protein, is biologically active by routine testing of the protein of fragment in a in vitro or in vivo assay for the biological activity of the MurD protein. For example, one can express N-terminal or C-terminal truncations, or internal additions or deletions, in host cells and test for their ability to catalyzing the ATP-dependent addition of D-glutamate to an alanyl residue of the UDP-N-acetylmuramyl-L-alanine precursor.

It is known that there is a substantial amount of redundancy in the various codons which code for specific amino acids. Therefore, this invention is also directed to those DNA sequences encode RNA comprising alternative codons

```
MetLysValIleSerAsnPheGlnAsnLysLysIleLeuIleLeuGlyLeuAlaLysSer

GlyGluAlaAlaAlaLysLeuLeuThrLysLeuGlyAlaLeuValThrValAsnAspSer

LysProPheAspGlnAsnProAlaAlaGlnAlaLeuLeuGluGluGlyIleLysValIle

CysGlySerHisProValGluLeuLeuAspGluAspPheGluTyrMetValLysAsnPro

GlyIleProTyrAspAsnProMetValLysArgAlaLeuAlaLysGluIleProIleLeu

ThrGluValGluLeuAlaTyrPheValSerGluAlaProIleIleGlyIleThrGlySer

AsnGlyLysThrThrThrThrThrMetIleAlaAspValLeuAsnAlaGlyGlyGlnSer

AlaLeuLeuSerGlyAsnIleGlyTyrProAlaSerLysValValGlnLysAlaIleAla

GlyAspThrLeuValMetGluLeuSerSerPheGlnLeuValGlyValAsnAlaPheArg

ProHisIleAlaValIleThrAsnLeuMetProThrHisLeuAspTyrHisGlySerPhe

GluAspTyrValAlaAlaLysTrpMetIleGlnAlaGlnMetThrGluSerAspTyrLeu

IleLeuAsnAlaAsnGlnGluIleSerAlaThrLeuAlaLysThrThrGlnAlaThrVal

IleProPheSerThrGlnLysValValAspGlyAlaTyrLeuLysAspGlyIleLeuTyr

PheLysGluGlnAlaIleIleAlaAlaThrAspLeuGlyValProGlySerHisAsnIle

GluAsnAlaLeuAlaThrIleAlaValAlaLysLeuSerGlyIleAlaAspAspIleIle

AlaGlnCysLeuSerHisPheGlyGlyValLysHisArgLeuGlnArgValGlyGlnIle

LysAspIleThrPheTyrAsnAspSerLysSerThrAsnIleLeuAlaThrGlnLysAla

LeuSerGlyPheAspAsnSerArgLeuIleLeuIleAlaGlyGlyLeuAspArgGlyAsn

GluPheAspAspLeuValProAspLeuLeuGlyLeuLysGlnMetIleIleLeuGlyGlu

SerAlaGluArgMetLysArgAlaAlaAsnLysAlaGluValSerTyrLeuGluAlaArg

AsnValAlaGluAlaThrGluLeuAlaPheLysLeuAlaGlnThrGlyAspThrIleLeu

LeuSerProAlaAsnAlaSerTrpAspMetTyrProAsnPheGluValArgGlyAspGlu

PheLeuAlaThrPheAspCysLeuArgGlyAspAla
```

The present invention also relates to biologically active fragments and mutant or polymorphic forms of MurD polypeptide sequence as set forth as SEQ ID NO: 2, including but not necessarily limited to amino acid substitutions, deletions, additions, amino terminal truncations and carboxy-terminal truncations such that these mutations pro-which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which can result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the ATP-dependent addition of D-glutamate to an alanyl residue of the UDP-N-acetylmuramyl-L-alanine precursor as compared to an unaltered MurD protein.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

As used herein, a "biologically active equivalent" or "functional derivative" of a wild-type MurD possesses a biological activity that is substantially similar to the biological activity of a wild type MurD. The term "functional derivative" is intended to include the "fragments," "mutants," "variants," "degenerate variants," "analogs" and "homologues" or to "chemical derivatives" of a wild type MurD protein. The term "fragment" is meant to refer to any polypeptide subset of wild-type MurD. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the MurD or MurD functional derivative. The term "variant" is meant to refer to a molecule substantially similar in structure and function to either the entire wild-type protein or to a fragment thereof. A molecule is "substantially similar" to a wild-type MurD-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full-length MurD protein or to a biologically active fragment thereof.

As used herein in reference to a MurD gene or encoded protein, a "polymorphic" MurD is a MurD that is naturally found in the population of Streptococci at large. A polymorphic form of MurD can have a different nucleotide sequence from the particular MurD genes and proteins disclosed herein. However, because of silent mutations, a polymorphic MurD gene can encode the same or different amino acid sequence as that disclosed herein. Further, some polymorphic forms MurD will exhibit biological characteristics that distinguish the form from wild-type MurD activity, in which case the polymorphic form is also a mutant.

A protein or fragment thereof is considered purified or isolated when it is obtained at least partially free from it's natural environment at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. We most prefer proteins that have been purified to homogeneity, that is, at least 10,000–100,000 fold.

Probes and Primers

Polynucleotide probes comprising full length or partial sequences of SEQ ID NO: 1 can be used to determine whether a cell or sample contains S. pyogenes MurD DNA or RNA. The effect of modulators that effect the transcription of the murD gene can be studied via the use of these probes. A preferred probe is a single stranded antisense probe having at least the full length of the coding sequence of MurD. It is also preferred to use probes that have less than the full length sequence, and contain sequences highly specific for S. pyogenes murD DNA or RNA. The identification of a sequence(s) for use as a specific probe is well known in the art and involves choosing a sequence(s) that is unique to the target sequence, or is highly specific thereto. It is preferred that polynucleotides that are probes have at least about 25 nucleotides, more preferably about 30 to 35 nucleotides. The longer probes are believed to be more specific for S. pyogenes murD gene(s) and RNAs and can be used under more stringent hybridization conditions. Longer probes can be used but can be more difficult to prepare synthetically, or can result in lower yields from a synthesis. Examples of sequences that are useful as probes or primers for S. pyogenes murD gene(s) are Primer A (sense) 5'-GGA TAG TGT GAG CTT AGA TGA AAG TGA TAA GT-3' nucleotides 1 to 32 of SEQ ID NO:1 and Primer B (antisense) 5'-CCA CCA CCT GTA AAT AAA ATC TTC TTA GGC ATT AGG CAT CTC C-3' nucleotides 1354 to 1397 of SEQ ID NO: 1. These primers are the first 32 (A) and the complement of the last 43 (B) nucleotides, respectively, of SEQ ID NO:1. However, one skilled in the art will recognize that these are only a few of the useful probe or primer sequences that can be derived from SEQ ID NO: 1.

Polynucleotides having sequences that are unique or highly specific for S. pyogenes murD can be used as primers in amplification reaction assays. These assays can be used in tissue typing as described herein. Additionally, amplification reactions employing primers derived from S. pyogenes murD sequences can be used to obtain amplified S. pyogenes murD DNA using the murD DNA of the cells as an initial template. The murD DNA so obtained can be a mutant or polymorphic form of *S. pyogenes* murD that differs from SEQ ID NO:1 by one or more nucleotides of the MurD open reading frame or sequences flanking the ORF. The differences can be associated with a non-defective naturally occurring form or with a defective form of MurD. Thus, polynucleotides of this invention can be used in identification of various *S. pyogenes* murD genes or the detection of an organism having a *S. pyogenes* murD gene. Many types of amplification reactions are known in the art and include, without limitation, Polymerase Chain Reaction, Reverse Transcriptase Polymerase Chain Reaction, Strand Displacement Amplification and Self-Sustained Sequence Reaction. Any of these or like reactions can be used with primers derived from SEQ ID NO:1.

Expression of MurD

A variety of expression vectors can be used to express recombinant MurD in host cells. Expression vectors are defined herein as DNA sequences that are required for the transcription of cloned DNA and the translation of their mRNAs in an appropriate host. Such vectors can be used to express bacteria DNA in a variety of hosts such as bacteria, bluegreen algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant MurD in bacterial cells. Commercially available bacterial expression vectors which are suitable for recombinant MurD expression include, but are not limited to pQE (Qiagen), pET11a or pET15b (Novagen), lambda gt11 (Invitrogen), and pKK223-3 (Pharmacia).

Alternatively, one can express murD DNA in cell-free transcription-translation systems, or murD RNA in cell-free translation systems. Cell-free synthesis of MurD can be in batch or continuous formats known in the art.

One can also synthesize MurD chemically, although this method is not preferred.

A variety of host cells can be employed with expression vectors to synthesize MurD protein. These can include *E. coli,* Bacillus, and Salmonella. Insect and yeast cells can also be appropriate.

Following expression of MurD in a host cell, MurD polypeptides can be recovered. Several protein purification procedures are available and suitable for use. MurD protein and polypeptides can be purified from cell lysates and extracts, or from culture medium, by various combinations of, or individual application of methods including ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophilic interactions. In some instances, protein denaturation and refolding steps can be employed. High performance liquid chromatography (HPLC) and reversed phase HPLC can also be useful. Dialysis can be used to adjust the final buffer composition.

The MurD protein itself is useful in assays to identify compounds that modulate the activity of the proteins—including compounds that inhibit the activity of the protein. The MurD protein is also useful for the generation of antibodies against the protein, structural studies of the protein, and structure/function relationships of the protein.

Modulators and Inhibitors of MurD

The present invention is also directed to methods for screening for compounds or molecules which modulate or inhibit the expression of DNA or RNA encoding a MurD protein. Compounds or molecules which modulate or inhibit MurD can be DNA, RNA, peptides, proteins, or non-proteinaceous organic compounds or molecules. Compounds that modulate the expression of DNA or RNA encoding MurD or are inhibitors of the biological function thereof can be detected by a variety of assays. The assay can be a simple "yes/no" assay to determine whether there is a change in expression or function. The assay can be made quantitative by comparing the expression or function of a test sample with the levels of expression or function in a standard sample, that is, a control. Kits containing MurD, antibodies to MurD, or modified MurD can be prepared by known methods for such uses.

The DNA molecules, RNA molecules, recombinant protein and antibodies of the present invention can be used to screen and measure levels of MurD. The recombinant proteins, DNA molecules, RNA molecules and antibodies lend themselves to the formulation of kits suitable for the detection and analysis of MurD. Such a kit would comprise a compartmentalized carrier suitable to hold in close confinement at least one container. The carrier would further comprise reagents such as recombinant MurD or anti-MurD antibodies suitable for detecting MurD. The carrier can also contain a means for detection such as labeled antigen or enzyme substrates or the like.

Pharmaceutical Compositions

Pharmaceutically useful compositions comprising inhibitors of MurD can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the inhibitor.

Therapeutic or diagnostic compositions of the invention are administered to an individual in amounts sufficient to treat or diagnose disorders. The effective amount can vary according to a variety of factors such as the individual's condition, weight, sex and age. Other factors include the mode of administration. The appropriate amount can be determined by a skilled physician.

The pharmaceutical compositions can be provided to the individual by a variety of routes such as subcutaneous, topical, oral and intramuscular.

The term "chemical derivative" describes a molecule that contains additional chemical moieties which are not normally a part of the base molecule. Such moieties can improve the solubility, half-life, absorption, etc. of the base molecule. Alternatively the moieties can attenuate undesirable side effects of the base molecule or decrease the toxicity of the base molecule. Examples of such moieties are described in a variety of texts, such as Remington's Pharmaceutical Sciences.

Compounds identified according to the methods disclosed herein can be used alone at appropriate dosages.

Alternatively, co-administration or sequential administration of other agents can be desirable.

The present invention also provides a means to obtain suitable topical, oral, systemic and parenteral pharmaceutical formulations for use in the methods of treatment of the present invention. The compositions containing compounds or molecules identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention can be administered in a single daily dose, or the total daily dosage can be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are presented by the way of illustration and, because various other embodiments will be apparent to those in the art, the following is not to be construed as a limitation on the scope of the invention:

EXAMPLE 1
General Materials and Methods

All reagents were purchased from Sigma Chemical Co, St. Louis, Mo., unless otherwise indicated. UDP-N-acetylmuramyl-L-alanine was synthesized and purified by a method known in the art (Jin, H., Emanuele, J. J., Jr., Fairman, R., Robertson, J. G., Hail, M. E., Ho, H.-T., Falk, P. and Villafranca, J. J, 1996, Structural studies of *Escherichia coli* UDP-N-acetylmuramate: L-alanine ligase, Biochemistry 35: 14423–14431).

DNA manipulations reagents and techniques.

Restriction endonucleases and T4 ligase were obtained from Gibco-BRL. Agarose gel electrophoresis and plasmid DNA preparations were performed according to published procedures (Sambrook, J., E. F. Fritsch, and T. Maniatis, 1989, Molecular cloning: a L, Laboratory Manual, 2nd ed. Cold Spring Harbor, N.Y.: Cold Spring Harbor Laboratory). Recombinant plasmids containing *S. pyogenes* murD were propagated in *E. coli* DH5a (Gibco-BRL, Rockville, Md.) prior to protein expression in *E. coli* BL21(DE3)/plysS (Novagen, Madison, Wis.). SDS-PAGE was performed with precast gels (Novagen). DNA sequences were determined using an automated ABI Prism DNA sequencer (Perkin-Elmer ABI, Foster City, Calif.).

EXAMPLE 2
Cloning of *Streptococcus pyogenes* murD

Genomic DNA from *S. pyogenes* (strain MB4439) was prepared from 100 ml late stationary phase culture in Brain Heart Infusion broth (Difco, Detroit, Mich.). Cells were washed with 0.2 M sodium acetate, suspended in 10 ml of TEG (100 mM Tris, pH 7, containing 10 mM EDTA and 25% glucose) and lysed by incubation with 200 μg of N-acetylmuramidase (Sigma) for 1 h at 37° C. Chromosomal DNA was purified from the cell lysate using a Qiagen (Santa Clarita, Calif.) genomic DNA preparation kit and following the manufacturers protocol. Briefly, the cell lysate was treated with protease K at 50° C. for 45 min, loaded onto an equilibrated Qiagen genomic tip, entered into the resin by centrifugation at 3000 rpm for 2 min. Following washing the genomic tip, the genomic DNA was eluted in distilled water and kept at 4° C. Approximately 50 ng genomic DNA was used as a template in PCR reactions to clone murD.

A murD homologue was localized in contig. sequence #306 of *S. pyogenes* genomic DNA sequence (Roe, B. A., S. Clifton, M. McShan and J. Ferretti. The Streptococcal genome sequencing project, University of Oklahoma, Oklahoma, USA) by searching the *S. pyogenes* genome for homology to *S. aureus* murD. The cloning of *S. aureus* murD is described in copending, commonly owned U.S. Application Ser. No. 60/064,183 filed Nov. 4, 1997, incorporated herein by reference in its entirety. The sequence of *S. aureus* murD is provided therein as SEQ ID NO:1.

Two oligonucleotide primers (Midland Certified Reagent, Midland, Tx.) complementary to sequences at the 5' and the 3' ends of *S. pyogenes* murD were used to clone this gene using Klentach advantage polymerase (Clontech, Palo Alto, Calif.). The primer nucleotide sequences were as follows: 5'-GG ATA GTG TGA GCT CAT ATG AAA GTG ATA AGT-3' (the first 34 nucleotides of SEQ ID NO: 1) and 5'-TTC AAG GTG ACA TGA CCT ACG GAT CCA CC-3' (the complement of the last 35 nucleotides of SEQ ID NO: 1). A PCR product representing *S. pyogenes* murD was verified by nucleotide sequence, digested with NdeI and BamHI, and cloned between the NdeI and BamHI sites of pET-15b, creating plasmid pSpyMurD. This plasmid was used for expression of the murD gene in *E. coli*.

The plasmid pSpyMurD has been deposited with the American Type Culture Collection on Oct. 31, 1997, under the terms of the Budapest Treaty for the Deposit of Microorganisms and has been designated as ATCC 98575. The deposited material is provided as a convenience and is not an admission that the deposited material is required to describe or practice the invention. The sequence of the polynucleotide of the deposit, and the encoded amino acid sequence, are incorporated herein by reference and are controlling in the event of a conflict with any description of the sequences provided in this specification or the associated drawings. A license may be required to make, use, sell or offer to sell the polynucleotide of the deposit or a protein of the amino acid sequence encoded by the polynucleotide. No such license is granted herein.

EXAMPLE 3
Sequence Analysis of *Streptococcus pyogenes* murD

The nucleotide sequence of murD, determined in both orientations, and the deduced amino acid sequence of the MurD protein is depicted in FIGS. 1A & 1B. Sequence comparison using the BLAST (1) algorithm against the GenBank database showed that, to varying degrees, the cloned region is homologous (% similar, % identical) to murD genes from *B. subtilis* (67%, 48%) and *S. aureus* murD (66%, 47%).

In addition to the several regions of homology that are conserved among MurD proteins from both Gram-positive and Gram-negative bacteria (FIGS. 2A & 2B), there are at least two regions that are particularly conserved among MurD proteins of Gram-negative bacteria. The first region is amino acid residues ValLysAsnProGlyIleProTyr (amino acids 77–84 of *S. pyogenes* murD; SEQ ID NO: 2) and the second region is amino acid residues GlyGlyLeuAspArgGlyAsnGluPheAsp (codons 354–363 of *S. pyogenes* murD; SEQ ID NO:2).

Multiple sequence alignments of MurC (Ikeda, M., M. Wachi, H. K. Jung, F. Ishino, and M. Matsuhashi, 1990, Nucleotide sequence involving murG and murC in the mra gene cluster of *Escherichia coli*. Nucleic Acids Res. 18:4014), MurD, MurE (Tao, J. S, and E. E., Ishiguro, 1989, Nucleotide sequence of the murE gene of *Escherichia coli*. Can. J. Microbiol. 35:1051–1054), and MurF (Parquet, C., D. Mengin-Lecreulx, B. Flouret, D. Mengin-Lecreulx, and J. van Heijenoort, 1989, Nucleotide sequence of the murF gene encoding the UDP-MurNAc-pentapeptide synthetase of *Escherichia coli.*, Nucleic Acids Res. 17:5379) proteins from several bacterial genera revealed four regions of homology with certain residues conserved amongst Mur ligases of both Gram-positive and Gram-negative bacteria (Eveland, S. S., D. L. Pompliano, and M. S. Anderson, 1997, Conditionally lethal *Escherichia coli* murein mutants contain point defects that map to regions conserved among murein and folyl poly-g-glutamate ligases: Identification of a ligase superfamily. Biochemistry, 36: 6223–6229, Ikeda, M., M. Wachi, H. K. Jung, F. Ishino, and M. Matsuhashi, 1990, Homology among MurC, MurD, MurE and MurF proteins in *Escherichia coli* and that between *E. coli* murG and a possible murG protein in *Bacillus subtilis*. J. Gen. Appl. Microbiol. 36: 179–187). The homologous regions may correlate with the catalytic functions of these enzymes (Eveland, et al., 1997). Most notable is the putative ATP binding region I that was found in MurF (Parquet, C., D. Mengin-Lecreulx, B. Flouret, D. Mengin-Lecreulx, and J. van Heijenoort, 1989, Nucleotide sequence of the murF gene encoding the UDP-MurNAc-pentapeptide synthetase of *Escherichia coli.*, Nucleic Acids Res. 17:5379) and is also conserved in *S. pyogenes* MurD protein GlySerAspGlyLysThrThr (codons 119 to 125, SEQ ID NO:2). While region I is an ATP-binding domain (Ikeda, et al., 1990), the function of the other homologous regions is unknown. Of these three other regions, only two of them appear to be present in *S. pyogenes* murD (FIG. 3). Region III, which contains two contiguous Asp residues, is not conserved in *S. pyogenes* MurD, although it is present in MurD of *B. subtilis*. Within regions I, II, and IV, the specific residues conserved in the known murein ligases are also present in *S. pyogenes* MurD (FIG. 3).

EXAMPLE 4
Overexpression, Purification and Enzymatic Activity of *Streptococcus pyogenes* MurD murD was cloned into the expression vector pET-15b (Novagen) as described above to create plasmid pSpyMurD. The pET-15b vector incorporates the 6×Histidine-tag into the protein construct to allow rapid purification of MurD by affinity chromatography. The pET (Plasmids for Expression by T7 RNA polymerase) plasmids are derived from pBR322 and designed for protein over-production in *E. coli*. The vector pET-15b contains the ampicillin resistance gene, ColE1 origin of replication in addition to T7 phage promoter and terminator. The T7 promoter is recognized by the phage T7 RNA polymerase but not by the *E. coli* RNA polymerase. A host *E. coli* strain such as BL21(DE3)pLysS is engineered to contain integrated copies of T7 RNA polymerase under the control of lacUV5 that is inducible by IPTG. Production of a recombinant protein in the *E. coli* strain BL21(DE3) pLysS occurs after expression of T7RNA polymerase is induced.

The pSpyMurD plasmid was introduced into the host strain BL21 DE3/pLysS (Novagen) for expression of His-tagged MurD. Colonies were grown at 37° C. in 100 ml of LB broth containing 100 mg/ml ampicillin and 32 µg/ml chloramphenicol. When cultures reached a cell density of $A_{600}$=0.5, cells were pelleted and then resuspended in M9ZB medium (Novagen) containing 1 mM IPTG. Cells were induced for 3 h at 30° C., pelleted at 3000 g, and frozen at −80° C.

Cultures containing either the recombinant plasmid pSpyMurD or the control plasmid vector, pET-15b were grown at 30° C. and induced with IPTG. Cells transformed with pSpyMurD contained an inducible protein of approximately 52 kDa, corresponding to the expected size of *S. pyogenes* MurD protein as shown by SDS-PAGE. There were no detectable protein bands after induction of cells transformed with the control plasmid vector, pET-15b.

Purification of Recombinant MurD Enzyme

The cell pellet from 100 ml of induced culture prepared as described above was resuspended in 10 ml BT buffer (50 mM bis-tris-propane, pH 8.0, containing 100 mM potassium chloride and 1% glycerol) at 4° C. Cells were lysed either by freeze-thaw or by French Press. After centrifugation, the supernatant was mixed with 15 ml of freshly prepared Talon resin and incubated for 30 min at room temp. The resin was washed twice by centrifugation with 25 ml of BT buffer at room temperature. Finally, the resin loaded into a column and washed with 20 ml of BT, pH 7.0, containing 5 mM imidazole. Protein was eluted with 20 ml of BT buffer pH 8.0, containing 100 mM imidazole. Fractions (0.5 ml) were collected and analyzed by SDS-Gel electrophoresis. Fractions containing MurD were pooled, cleaved with thrombin (20 units/mg of His-tagged MurD) to remove the histidine tag. Finally the MurD protein was purified on Superdex 75 size exclusion column and eluted in 10 mM tris, pH 7.4, 150 mM NaCl and dialyzed in 100 mM MOPS, pH 7.5, using a Slide-A-Lyzer (Pierce, Rockford, Ill.). This resulted in a partially purified preparation of *S. pyogenes* MurD protein that could be used in activity assays. The protein may be purified further, if desired, using methods known in the art.

Assay for Activity of MurD Enzyme

The ATP-dependent MurD activity was assayed by monitoring the formation of product ADP using the pyruvate kinase and lactate dehydrogenase coupled enzyme assay. The reaction was monitored spectrophotometrically.

Typically, the assay contained 100 mM BIS-TRIS-propane, pH 8.0, 200 µM NADH, 1 mM ATP, 20 mM PEP, 5 mM $MgCl_2$, 1 mM DTT, 350 µM UDP-N-acetyl-muramyl-L-alanine, 1 mM D-glutamate, 33 units/ml of pyruvate kinase and 1660 units/ml of lactate dehydrogenase in a final volume of 200 or 400 µL. The mixture was incubated at 25° C. for 5 min and the reaction initiated by the addition of 1–10 μg of MurD. ADP formation was monitored by the decrease in absorbance at 340 nm as a function of time using a Molecular Devices SpectramaxPlus microtiterplate spectrophotomer (for 200 μl assays) or a Hewlett-Packard HP8452A spectrophotometer equipped with a circulating water bath (for 400 μl assays). Rates were calculated from the linear portions of the progress curves using the extinction coefficient for NADH, e=6220 cm$^{-1}$ M$^{-1}$. One unit of MurD activity is equal to 1 μmol of ADP formed per min at 25° C. MurD activity co-eluted with a ~52 kDa protein.

TABLE 1

Specific activities of recombinant MurD from *E. coli* and *S. pyogenes*.

| Species | protein used (mg) | units (μmole/min)[1] | Specific activity (μmol/min mg) |
|---|---|---|---|
| *E. coli*[2] | 0.00277 | 0.012250 | 4.40 |
| *S. pyogenes*[3] | 0.00137 | 0.00017 | 0.13 |

[1]Concentration of UDP-N-acetylmuramyl-L-ala, D-glutamate, ATP were 350 μM, 1 mM, and 1 mM, respectively. Volume of the reactions were 200 μl at 25° C.
[2]*E. coli* Mur D was prepared described in Pratviel-Sosa, et al. (1991).
[3]*S. pyogenes* MurD was partially purified as described above.

Assays have been conducted using 120 and 350 μM UDP-N-acetyl-muramyl-L-alanine. However, it has been observed that at the higher level of 350 μM UDP-N-acetyl-muramyl-L-alanine, substrate inhibition of the *E. coli* MurD occurs. At the lower level, the specific activity of the *E. coli* enzyme can be in the area of 8 units/mg. It is unclear whether the *S. pyogenes* enzyme is similarly inhibited.

EXAMPLE 5
Screening for Inhibitors of MurD

One assay for the measurement of the activity of MurD is provided in Example 4. That assay, and other assays for MurD activity can be adapted for screening assays to detect inhibitors of MurD. For inhibition studies, inhibitors in DMSO are added at the desired concentration to the assay mixture. In a separate, control reaction, only DMSO is added to the assay mixture. The reactions are initiated by the addition of enzyme (MurD). Rates were calculated as described above. Relative activities were calculated from the equation 1:

$$\text{relative activity} = \text{rate with inhibitor/rate without inhibitor.} \quad (1)$$

Inhibition constant (IC$_{50}$) values were determined from a range of inhibitor concentrations and calculated from the equation 2 using Sigma Plot (Jandel Scientific).

$$\text{relative activity} = 1/(1+[I]/IC_{50}) \quad (2)$$

We prefer inhibitors of MurD that result in relative activities of the MurD enzyme of at least less than 75%, more preferably, 25–50% or 10–25%. We most prefer inhibitors resulting in relative activities of less than 20%, particularly less than 10% of the activity or Mur D in the absence of the inhibitor.

We also prefer inhibitors that effectively lower the relative activity of MurD when present at very low levels.

EXAMPLE 8
Pharmaceutical Compositions

An appropriate amount of an inhibitor of MurD is formulated in a pharmaceutically acceptable carrier, in an appropriate dosage form.

EXAMPLE 9
Therapy Using Inhibitors of MurD

A patient presenting with an indication of infection with a microorganism susceptible to inhibitors of MurD, e.g., gram positive organisms, including *S. pyogenes,* can be treated by administration of inhibitors of MurD. Physicians skilled in the art are familiar with administering therapeutically effective amounts of inhibitors of microbial enzymes. Such skilled persons can readily determine an appropriate dosing scheme to achieve a desired therapeutic effect.

REFERENCES

Altschul, S. F., W. Gish, W. Miller, E. Myers, and D. J. Lipman, 1990, Basic local alignment search tool. J. Mol. Biol. 215:403–410.

Blanot, D., A. Kretsovali, M. Abo-Ghalia, D. Mengin-Lecreulx, and J. van Heijenoort, 1983, Synthesis of analogues of precursors of bacterial peptidoglycan. p. 311–314. In peptides. Blaha, K. and P. Malon, eds. PP311–314. Walter de Gryter and Co. Berlin, N.Y Daniel, R. A., and J. Errington, 1993, DNA sequence of the murE-murD region of *Bacillus subtilis* 168, J. Gen. Microbiol. 139:361–370.

Eveland, S. S., D. L. Pompliano, and M. S. Anderson, 1997, Conditionally lethal *Escherichia coli* murein mutants contain point defects that map to regions conserved among murein and folyl poly-g-glutamate ligases: Identification of a ligase superfamily. Biochemistry, 36:6223–6229.

Flouret, B., D. Mengin-Lecreulx, and J. van Heijenoort, 1981, Reverse-phase high-pressure liquid chromatography of Uridine Diphosphate N-Acetylmuramyl peptide precursors of bacterial cell wall peptidoglycan, Anal. Biochem. 114:59–63.

Henriques, A. O. de Lencaster, H. and P. J. Piggot, 1992, A *Bacillus subtilis* morphogene cluster that includes spoVE is homologous to the mra region of *Escherichia coli.* Biochimie. 74: 735–748.

Ikeda, M., M. Wachi, F. Ishino, and M. Matsuhashi, 1990, Nucleotide sequence involving murD and an open reading frame ORF-Y spacing murF and ftsW in *Escherichia coli.* Nucleic Acids Res. 18:1058.

Ikeda, M., M. Wachi, H. K. Jung, F. Ishino, and M. Matsuhashi, 1990, Nucleotide sequence involving murG and murC in the mra gene cluster of *Escherichia coli.* Nucleic Acids Res. 18:4014.

Ikeda, M., M. Wachi, H. K. Jung, F. Ishino, and M. Matsuhashi, 1990, Homology among MurC, MurD, MurE and MurF proteins in *Escherichia coli* and that between *E. coli* murG and a possible murG protein in *Bacillus subtilis.* J. Gen. Appl. Microbiol. 36: 179–187.

Ito, E. and J. L. Strominger, 1962, Enzymatic synthesis of the peptide in bacterial uridine nucleotides: Enzymatic addition of L-alanine, D-glutamic acid, and L-lysine. J. Biol. Chem. 237: 2689–2695.

Ito E. and J. L. Strominger, 1973, Enzymatic synthesis of the peptide in bacterial uridine nucleotides: Comparative biochemistry, J. Biol. Chem. 248: 3131–3136.

Jin, H., Emanuele, J. J., Jr., Fairman, R., Robertson, J. G., Hail, M. E., Ho, H.-T., Falk, P. and Villafranca, J. J., 1996, Structural studies of *Escherichia coli* UDP-N-acetylmuramate: L-alanine ligase, Biochemistry 35: 14423–14431.

Lugtenberg, E. J. J., 1972, Studies on *Escherichia coli* enzymes involved in the synthesis of Uridine Diphosphate-N-Acetyl-Muramyl-pentapeptide. J. Bacteriol. 110:26–34.

Mengin-Lecreulx, D., B. Flouret, and J. van Heijenoort, 1982, Cytoplasmic steps of peptidoglycan synthesis in *Escherichia coli.* J. Bacteriol. 151: 1109–1117.

Mengin-Lecreulx, D., C Michaud, C. Richaud, D. Blanot and J. van Heijenoort, 1988, Incorporation of LL-diaminopimelic acid into peptidoglycan of *Escherichia coli* mutants lacking diaminopimelate epimerase encoded by dapF, J. Bacteriol. 170:2031–2039.

Mengin-Lecreulx, D., C Parquet, L. Desviat, J. Pla, B. Flouret, J. Ayala and and J. van Heijenoort, 1989, Organization of the murE-murG region of *Escherichia coli:* Identification of the murD gene encoding the D-glutamic-acid-adding enzyme, J. Bacteriol. 171: 6126–6134.

Mengin-Lecreulx, D. and J. van Heijenoort, 1990, Nucleotide sequence of the murD gene encoding the UDP-MurNAc-L-Ala-D-Glu synthetase of *Escherichia coli.* Nucleic Acids Research 18:183.

Michaud, C. D. Blanot, B. Flouret, and J. van Heijenoort, 1987, Partial purification and specificity studies of the D-glutamate-adding and D-alanyl-D-alanine-adding enzymes from *Escherichia coli* K12. Eur. J. Biochem. 166: 631–637.

Michaud, C., C., Parquet, B. Flouret, D. Blanot, and J. van Heijenoort, 1990, Revised interpretation of the sequence containing the murE gene encoding the UDP-N-acetyl-muramyl-tripeptide synthetase of *Escherichia coli.* Biochem. J. 269:277–280.

Nathenson, S. G., J. L. Strominger, and E. Ito, 1964, Enzymatic synthesis of the peptide in bacterial uridine nucleotides: purification and properties of D-Glutamic acid-adding enzyme, J. Biol. Chem. 239: 1773–1776.

Parquet, C., D. Mengin-Lecreulx, B. Flouret, D. Mengin-Lecreulx, and J. van Heijenoort, 1989, Nucleotide sequence of the murF gene encoding the UDP-MurNAc-pentapeptide synthetase of *Escherichia coli.,* Nucleic Acids Res. 17:5379.

Pratviel-Sosa F, D. Mengin-Lecreulx and J. van Heijenoort, 1991, Over-production, purification and properties of the uridine diphosphate N-acetylmuramoyl-L-alanine:D-glutamate ligase from *Escherichia coli.* Eur. J. Biochem. 202 (3):1169–1176.

Roe, B. A., S. Clifton, M. McShan and J. Ferretti. The Streptococcal genome sequencing project, University of Oklahoma, Okla., USA.

Rogers, H. J., H. R. Perkins, and J. B. Ward, 1980, Biosynthesis of peptidoglycan. p. 239–297. In Microbial cell walls and membranes. Chapman & Hall Ltd. London.

Sambrook, J., E. F. Fritch, and T. Maniatis, 1989, Molecular cloning: a L, Laboratory Manual, 2nd edn. Cold Spring Harbor, N.Y.: Cold Spring Harbor Laboratory.

Schleifer, K. H. and O. Kandler, 1972, Peptidoglycan types of bacterial cell walls and their taxonomic implications. Bacteriol. Review. 36:407–477.

Tanner, M. E., S. Vaganay, van Heijenoort, J., and D. Blanot, 1996, Phosphinate Inhibitors of the D-Glutamic Acid-Adding Enzyme of Peptidoglycan Biosynthesis. J. Org. Chem. 61:1756–1760.

Tao, J. S, and E. E., Ishiguro, 1989, Nucleotide sequence of the murE gene of *Escherichia coli.* Can. J. Microbiol. 35:1051–1054.

---

What is claimed:

1. An isolated and purified polynucleotide fragment selected from the group consisting of:
   (a) a polynucleotide encoding a polypeptide having an amino acid sequence of SEQ ID NO:2, and
   (b) a polynucleotide which is complementary to the polynucleotide of (a).

2. The polynucleotide of claim 1 comprising the nucleotide sequence of SEQ ID NO:1.

3. A polynucleotide that is an expression vector comprising a polynucleotide of claim 1.

4. A host cell comprising the expression vector of claim 3.

5. A process for expressing a MurD protein of *Streptococcus pyogenes* in a recombinant host cell, comprising:
   (a) transfecting a suitable host cell with an expression vector of claim 3; and,
   (b) culturing the host cell of step (a) in conditions under which allow expression of said the MurD protein from said expression vector.

6. A substantially purified polypeptide having an amino acid sequence of SEQ ID NO:2.

* * * * *

SEQUENCE LISTING

<160> NUMBER OF SEQ ID NOS: 6

<210> SEQ ID NO 1
<211> LENGTH: 1407
<212> TYPE: DNA
<213> ORGANISM: Streptococcus pyogenes murD

<400> SEQUENCE: 1

```
ggatagtgtg agcttagatg aaagtgataa gtaattttca aaacaaaaaa atattaatat      60
tggggttagc caaatcgggc gaagcagcag caaaattatt gaccaaactt ggtgctttag     120
tgactgttaa tgatagtaaa ccatttgacc aaaatccagc ggcacaagcc ttgttggaag     180
aggggattaa ggtcatttgt ggtagccacc cagtagaatt attagatgag gactttgagt     240
acatggttaa aaaccctggg attccttatg ataatcctat ggttaaacgc gcccttgcaa     300
aggaaattcc catcttgact gaagtagaat tggcttattt cgtatctgaa gcgcctatta     360
tcgggattac aggatcaaac gggaagacaa ccacaacgac aatgattgcc gatgttttga     420
atgctggcgg gcaatctgca ctcttatctg gaaacattgg ttatcctgct tcaaaagttg     480
ttcaaaaagc aattgctggt gatactttgg tgatggaatt gtcctctttt caattagtgg     540
gagtgaatgc ttttcgccct catattgctg tcatcactaa tttaatgccg actcatctgg     600
actatcatgg cagttttgag gattatgttg ctgctaaatg gatgattcaa gctcagatga     660
cagaatcaga ctaccttatt ttaaatgcta atcaagagat ttcagcaact ctagctaaga     720
ccacccaagc aacagtgatt cctttttcaa ctcaaaaagt ggttgatgga gcttatctga     780
```

-continued

```
aggatggaat actctatttt aaagaacagg cgattatagc tgcaactgac ttaggtgtcc      840
caggtagcca caacattgaa aatgccctag caactattgc agttgccaag ttatctggta      900
ttgctgatga tattattgcc cagtgccttt cacattttgg aggcgttaaa catcgtttgc      960
aacgggttgg tcaaatcaaa gatattacct tctacaatga cagtaagtca accaatattt     1020
tagccactca aaaagcttta tcaggttttg ataacagtcg cttgattttg attgctggcg     1080
gtctagatcg tggcaatgaa tttgacgatt tggtgccaga ccttttagga cttaagcaga     1140
tgattatttt gggagaatcc gcagagcgta tgaagcgagc tgctaacaaa gcagaggtct     1200
cttatcttga agctagaaat gtggcagaag caacagagct tgcttttaag ctggcccaaa     1260
caggcgatac tatcttgctt agcccagcta atgctagctg ggatatgtat cctaattttg     1320
aggttcgtgg ggatgaattt ttggcaacct ttgattgttt aagaggagat gcctaatgcc     1380
taagaagatt ttatttacag gtggtgg                                         1407
```

<210> SEQ ID NO 2
<211> LENGTH: 452
<212> TYPE: PRT
<213> ORGANISM: Streptococcus pyogenes MurD

<400> SEQUENCE: 2

```
Met Lys Val Ile Ser Asn Phe Gln Asn Lys Lys Ile Leu Ile Leu Gly
1               5                   10                  15

Leu Ala Lys Ser Gly Glu Ala Ala Lys Leu Leu Thr Lys Leu Gly
            20                  25                  30

Ala Leu Val Thr Val Asn Asp Ser Lys Pro Phe Asp Gln Asn Pro Ala
        35                  40                  45

Ala Gln Ala Leu Leu Glu Glu Gly Ile Lys Val Ile Cys Gly Ser His
    50                  55                  60

Pro Val Glu Leu Leu Asp Glu Asp Phe Glu Tyr Met Val Lys Asn Pro
65                  70                  75                  80

Gly Ile Pro Tyr Asp Asn Pro Met Val Lys Arg Ala Leu Ala Lys Glu
                85                  90                  95

Ile Pro Ile Leu Thr Glu Val Glu Leu Ala Tyr Phe Val Ser Glu Ala
            100                 105                 110

Pro Ile Ile Gly Ile Thr Gly Ser Asn Gly Lys Thr Thr Thr Thr Thr
        115                 120                 125

Met Ile Ala Asp Val Leu Asn Ala Gly Gly Gln Ser Ala Leu Leu Ser
    130                 135                 140

Gly Asn Ile Gly Tyr Pro Ala Ser Lys Val Val Gln Lys Ala Ile Ala
145                 150                 155                 160

Gly Asp Thr Leu Val Met Glu Leu Ser Ser Phe Gln Leu Val Gly Val
                165                 170                 175

Asn Ala Phe Arg Pro His Ile Ala Val Ile Thr Asn Leu Met Pro Thr
            180                 185                 190

His Leu Asp Tyr His Gly Ser Phe Glu Asp Tyr Val Ala Ala Lys Trp
        195                 200                 205

Met Ile Gln Ala Gln Met Thr Glu Ser Asp Tyr Leu Ile Leu Asn Ala
    210                 215                 220

Asn Gln Glu Ile Ser Ala Thr Leu Ala Lys Thr Thr Gln Ala Thr Val
225                 230                 235                 240

Ile Pro Phe Ser Thr Gln Lys Val Val Asp Gly Ala Tyr Leu Lys Asp
                245                 250                 255

Gly Ile Leu Tyr Phe Lys Glu Gln Ala Ile Ile Ala Ala Thr Asp Leu
```

-continued

```
                260                 265                 270
Gly Val Pro Gly Ser His Asn Ile Glu Asn Ala Leu Ala Thr Ile Ala
            275                 280                 285
Val Ala Lys Leu Ser Gly Ile Ala Asp Asp Ile Ile Ala Gln Cys Leu
        290                 295                 300
Ser His Phe Gly Gly Val Lys His Arg Leu Gln Arg Val Gly Gln Ile
305                 310                 315                 320
Lys Asp Ile Thr Phe Tyr Asn Asp Ser Lys Ser Thr Asn Ile Leu Ala
                325                 330                 335
Thr Gln Lys Ala Leu Ser Gly Phe Asp Asn Ser Arg Leu Ile Leu Ile
            340                 345                 350
Ala Gly Gly Leu Asp Arg Gly Asn Glu Phe Asp Asp Leu Val Pro Asp
        355                 360                 365
Leu Leu Gly Leu Lys Gln Met Ile Ile Leu Gly Glu Ser Ala Glu Arg
    370                 375                 380
Met Lys Arg Ala Ala Asn Lys Ala Glu Val Ser Tyr Leu Glu Ala Arg
385                 390                 395                 400
Asn Val Ala Glu Ala Thr Glu Leu Ala Phe Lys Leu Ala Gln Thr Gly
                405                 410                 415
Asp Thr Ile Leu Leu Ser Pro Ala Asn Ala Ser Trp Asp Met Tyr Pro
            420                 425                 430
Asn Phe Glu Val Arg Gly Asp Glu Phe Leu Ala Thr Phe Asp Cys Leu
        435                 440                 445
Arg Gly Asp Ala
    450

<210> SEQ ID NO 3
<211> LENGTH: 438
<212> TYPE: PRT
<213> ORGANISM: Escherichia coli MurD

<400> SEQUENCE: 3

Met Ala Asp Tyr Gln Gly Lys Asn Val Val Ile Ile Gly Leu Gly Leu
1               5                   10                  15
Thr Gly Leu Ser Cys Val Asp Phe Phe Leu Ala Arg Gly Val Thr Pro
            20                  25                  30
Arg Val Met Asp Thr Arg Met Thr Pro Pro Gly Leu Asp Lys Leu Pro
        35                  40                  45
Glu Ala Val Glu Arg His Thr Gly Ser Leu Asn Asp Glu Trp Leu Met
    50                  55                  60
Ala Ala Asp Leu Ile Val Ala Ser Pro Gly Ile Ala Leu Ala His Pro
65                  70                  75                  80
Ser Leu Ser Ala Ala Ala Asp Ala Gly Ile Glu Ile Val Gly Asp Ile
                85                  90                  95
Glu Leu Phe Cys Arg Glu Ala Gln Ala Pro Ile Val Ala Ile Thr Gly
            100                 105                 110
Ser Asn Gly Lys Ser Thr Val Thr Thr Leu Val Gly Glu Met Ala Lys
        115                 120                 125
Ala Ala Gly Val Asn Val Gly Val Gly Gly Asn Ile Gly Leu Pro Ala
    130                 135                 140
Leu Met Leu Leu Asp Asp Glu Cys Glu Leu Tyr Val Leu Glu Leu Ser
145                 150                 155                 160
Ser Phe Gln Leu Glu Thr Thr Ser Ser Leu Gln Ala Val Ala Ala Thr
                165                 170                 175
```

-continued

```
Ile Leu Asn Val Thr Glu Asp His Met Asp Arg Tyr Pro Phe Gly Leu
            180                 185                 190

Gln Gln Tyr Arg Ala Ala Lys Leu Arg Ile Tyr Glu Asn Ala Lys Val
            195                 200                 205

Cys Val Val Asn Ala Asp Asp Ala Leu Thr Met Pro Ile Arg Gly Ala
            210                 215                 220

Asp Glu Arg Cys Val Ser Phe Gly Val Asn Met Gly Asp Tyr His Leu
225                 230                 235                 240

Asn His Gln Gln Gly Glu Thr Trp Leu Arg Val Lys Gly Glu Lys Val
            245                 250                 255

Leu Asn Val Lys Glu Met Lys Leu Ser Gly Gln His Asn Tyr Thr Asn
            260                 265                 270

Ala Leu Ala Ala Leu Ala Leu Ala Asp Ala Ala Gly Leu Pro Arg Ala
            275                 280                 285

Ser Ser Leu Lys Ala Leu Thr Thr Phe Thr Gly Leu Pro His Arg Phe
            290                 295                 300

Glu Val Val Leu Glu His Asn Gly Val Arg Trp Ile Asn Asp Ser Lys
305                 310                 315                 320

Ala Thr Asn Val Gly Ser Thr Glu Ala Ala Leu Asn Gly Leu His Val
            325                 330                 335

Asp Gly Thr Leu His Leu Leu Gly Gly Asp Gly Lys Ser Ala Asp
            340                 345                 350

Phe Ser Pro Leu Ala Arg Tyr Leu Asn Gly Asp Asn Val Arg Leu Tyr
            355                 360                 365

Cys Phe Gly Arg Asp Gly Ala Gln Leu Ala Ala Leu Arg Pro Glu Val
            370                 375                 380

Ala Glu Gln Thr Glu Thr Met Glu Gln Ala Met Arg Leu Leu Ala Pro
385                 390                 395                 400

Arg Val Gln Pro Gly Asp Met Val Leu Leu Ser Pro Ala Cys Ala Ser
            405                 410                 415

Leu Asp Gln Phe Lys Asn Phe Glu Gln Arg Gly Asn Glu Phe Ala Arg
            420                 425                 430

Leu Ala Lys Glu Leu Gly
            435

<210> SEQ ID NO 4
<211> LENGTH: 437
<212> TYPE: PRT
<213> ORGANISM: Haemophilus inflenzae MurD

<400> SEQUENCE: 4

Met Asn Ala Tyr Gln Asn Lys Asn Ile Thr Ile Ile Gly Leu Gly Lys
1               5                   10                  15

Thr Gly Leu Ser Cys Val Asp Tyr Leu Leu Ser Gln Gln Ala Asn Ile
            20                  25                  30

Arg Val Ile Asp Thr Arg Lys Asn Pro Thr Gly Ile Asp Lys Leu Pro
            35                  40                  45

Gln Asn Ile Pro Leu His Thr Gly Ser Leu Asn Gln Glu Trp Leu Leu
            50                  55                  60

Glu Ser Asp Met Ile Val Ile Ser Pro Gly Leu Ala Val Lys Thr Pro
65                  70                  75                  80

Glu Ile Gln Thr Ala Leu Lys Ala Gly Val Glu Val Ile Gly Asp Ile
            85                  90                  95

Glu Leu Phe Cys Arg Ala Ala Thr Lys Pro Ile Val Gly Ile Thr Gly
            100                 105                 110
```

-continued

```
Ser Asn Gly Lys Ser Thr Val Thr Leu Val Tyr Glu Met Ala Lys
            115                 120                 125
Ala Ala Gly Val Lys Val Gly Met Gly Gly Asn Ile Gly Ile Pro Ala
    130                 135                 140
Leu Ser Leu Leu Asn Glu Asp Cys Glu Leu Tyr Val Leu Glu Leu Ser
145                 150                 155                 160
Ser Phe Gln Leu Glu Thr Thr Tyr Ser Leu Lys Ala Ala Ala Thr
                165                 170                 175
Val Leu Asn Val Thr Glu Asp His Met Asp Arg Tyr Met Asp Leu Glu
            180                 185                 190
Asp Tyr Arg Gln Ala Lys Leu Arg Ile Tyr His Asn Ala Lys Val Gly
            195                 200                 205
Val Leu Asn Asn Glu Asp Arg Leu Thr Phe Gly Glu Asn Glu Asn Gln
            210                 215                 220
Ala Lys His Thr Val Ser Phe Ala Glu Asn Ser Ala Asp Tyr Trp Leu
225                 230                 235                 240
Lys Thr Glu Asn Gly Lys Gln Tyr Leu Met Val Lys Asp Glu Val Ile
                245                 250                 255
Leu Pro Cys Glu Glu Ala Thr Leu Val Gly Arg His Asn Tyr Met Asn
            260                 265                 270
Ile Leu Ala Ala Thr Ala Leu Ala Gln Ala Ile Gly Ile Asn Leu Asp
            275                 280                 285
Ser Ile Arg Thr Ala Leu Arg His Phe Lys Gly Leu Asp His Arg Phe
            290                 295                 300
Gln Leu Val His Gln Ala Asn Gly Ile Arg Trp Ile Asn Asp Ser Lys
305                 310                 315                 320
Ala Thr Asn Val Gly Ser Thr Val Ala Ala Leu Ala Gly Leu Tyr Ile
                325                 330                 335
Glu Gly Lys Leu His Leu Leu Gly Gly Asp Gly Lys Gly Ala Asp
            340                 345                 350
Phe Ser Glu Leu Ala Glu Leu Ile Asn Gln Pro His Ile Ile Cys Tyr
            355                 360                 365
Cys Phe Gly Arg Asp Gly Ala Leu Leu Ala Lys Phe Ser Ser Gln Ser
370                 375                 380
Tyr Leu Phe Asp Thr Met Glu Gln Ala Ile Glu Phe Leu Arg Pro Thr
385                 390                 395                 400
Leu Gln Ser Gly Asp Met Val Leu Leu Ser Pro Ala Cys Ala Ser Leu
            405                 410                 415
Asp Gln Phe Ala Ser Phe Glu Lys Arg Gly Glu Glu Phe Thr His Leu
            420                 425                 430
Ala Gln Cys Leu Thr
        435

<210> SEQ ID NO 5
<211> LENGTH: 451
<212> TYPE: PRT
<213> ORGANISM: Bacillus subtilis MurD

<400> SEQUENCE: 5

Val Glu Asn Asp Gln Phe Leu Gln Lys Gln His Phe Leu Ile Leu Gly
1               5                  10                  15
Leu Ala Lys Ser Gly Tyr Ala Ala Ala Ser Ile Leu His Glu Lys Gly
            20                  25                  30
Ile Tyr Val Ala Val Asn Asp Gln Lys Pro Phe Glu Glu Asn Glu Pro
```

```
                35                  40                  45
Ala Gln Lys Leu Ser Glu Lys Gly Ile Glu Val Val Cys Gly Glu His
 50                  55                  60

Pro Val Ser Leu Phe Asp Gln His Gln Ile Thr Ile Leu Ile Lys Asn
 65                  70                  75                  80

Pro Gly Ile Pro Tyr Glu Asn Ile Met Val Gln Glu Ala Glu Lys Arg
                 85                  90                  95

Gly Ile Pro Val Trp Thr Glu Ile Glu Leu Ala Tyr Tyr Leu Thr Ser
                100                 105                 110

Ala Lys Phe Ile Gly Ile Thr Gly Ser Asn Gly Lys Thr Thr Thr Thr
            115                 120                 125

Thr Leu Ile Tyr Glu Met Leu Lys Ala Asp Ser Gln Lys Ala Leu Ile
    130                 135                 140

Ala Gly Asn Ile Gly Thr Val Ala Ser Glu Val Ala Tyr His Ala Asp
145                 150                 155                 160

Gly Asp Glu Trp Ile Val Thr Glu Leu Ser Ser Phe Gln Leu Met Gly
                165                 170                 175

Thr His Ala Phe Arg Pro Glu Ile Ser Leu Ile Leu Asn Val Phe Asp
            180                 185                 190

Ala His Leu Asp Tyr His His Thr Arg Glu Asn Tyr Glu Lys Ala Lys
    195                 200                 205

Gln Lys Val Tyr Leu His Gln Thr Ala Ser Asp Lys Ala Ile Val Asn
    210                 215                 220

Gln Asp Asp Glu Thr Val Val Arg Leu Ala Glu Ala Gly Lys Ala Glu
225                 230                 235                 240

Ile Val Pro Phe Ser Val Ser Lys Thr Leu Glu Gln Gly Ala Tyr Val
                245                 250                 255

Lys Asp Ser Met Ile Met Phe Asn Gly Glu Ala Ile Leu Pro Leu Glu
            260                 265                 270

Glu Val Val Leu Pro Gly Ala His Asn Leu Glu Asn Ile Leu Ala Ala
    275                 280                 285

Ile Ala Val Val Lys Thr Ala Gly Ala Ser Asn Glu Ala Val Lys Lys
    290                 295                 300

Val Leu Thr Ser Phe Thr Gly Val Lys His Arg Leu Gln Tyr Val Thr
305                 310                 315                 320

Thr Val Asn Gly Arg Lys Phe Tyr Asn Asp Ser Lys Ala Thr Asn Ile
                325                 330                 335

Leu Ala Thr Ser Lys Ala Leu Ser Ala Phe Asp Lys Pro Val Ile Leu
            340                 345                 350

Leu Ala Gly Gly Leu Asp Arg Gly Asn Gly Phe Asp Asp Leu Lys Pro
    355                 360                 365

Tyr Met Lys His Val Lys Ala Val Leu Thr Phe Gly Gln Thr Ala Pro
    370                 375                 380

Lys Leu Glu Lys Leu Gly Asn Glu Leu Gly Ile Gln His Val Lys Arg
385                 390                 395                 400

Val Asp Asn Val Glu Gln Ala Val Ser Ala Ala Phe Ala Leu Ser Asn
                405                 410                 415

Glu Gly Asp Val Ile Leu Leu Ser Pro Ala Cys Ala Ser Trp Asp Gln
            420                 425                 430

Phe Lys Thr Phe Glu Glu Arg Gly Asp Met Phe Ile Asp Ala Val His
    435                 440                 445

Met Leu Lys
    450
```

<210> SEQ ID NO 6
<211> LENGTH: 449
<212> TYPE: PRT
<213> ORGANISM: Staphylococcus aureus MurD

<400> SEQUENCE: 6

| Met | Leu | Asn | Tyr | Thr | Gly | Leu | Glu | Asn | Lys | Asn | Val | Leu | Val | Val | Gly |
|-----|-----|-----|-----|-----|-----|-----|-----|-----|-----|-----|-----|-----|-----|-----|-----|
| 1 | | | | 5 | | | | | 10 | | | | | 15 | |

Leu Ala Lys Ser Gly Tyr Glu Ala Ala Lys Leu Leu Ser Lys Leu Gly
            20                  25                  30

Ala Asn Val Thr Val Asn Asp Gly Lys Asp Leu Ser Gln Asp Ala His
        35                  40                  45

Ala Lys Asp Leu Glu Ser Met Gly Ile Ser Val Val Ser Gly Ser His
50                  55                  60

Pro Leu Thr Leu Asp Asn Asn Pro Ile Ile Val Lys Asn Pro Gly
65                  70                  75                  80

Ile Pro Tyr Thr Val Ser Ile Ile Asp Glu Ala Val Lys Arg Gly Leu
                85                  90                  95

Lys Ile Leu Thr Glu Val Glu Leu Ser Tyr Leu Ile Ser Glu Ala Pro
                100                 105                 110

Ile Ile Ala Val Thr Gly Thr Asn Gly Lys Thr Thr Val Thr Ser Leu
            115                 120                 125

Ile Gly Asp Met Phe Lys Lys Ser Arg Leu Thr Gly Arg Leu Ser Gly
130                 135                 140

Asn Ile Gly Tyr Val Ala Ser Lys Val Ala Gln Glu Val Lys Pro Thr
145                 150                 155                 160

Asp Tyr Leu Val Thr Glu Leu Ser Ser Phe Gln Leu Leu Gly Ile Glu
                165                 170                 175

Lys Tyr Lys Pro His Ile Ala Ile Ile Thr Asn Ile Tyr Ser Ala His
                180                 185                 190

Leu Asp Tyr His Glu Asn Leu Glu Asn Tyr Gln Asn Ala Lys Lys Gln
            195                 200                 205

Ile Tyr Lys Asn Gln Thr Glu Glu Asp Tyr Leu Ile Cys Asn Tyr His
210                 215                 220

Gln Arg Gln Val Ile Glu Ser Glu Glu Leu Lys Ala Lys Thr Leu Tyr
225                 230                 235                 240

Phe Ser Thr Gln Gln Glu Val Asp Gly Ile Tyr Ile Lys Asp Gly Phe
                245                 250                 255

Ile Val Tyr Lys Gly Val Arg Ile Ile Asn Thr Glu Asp Leu Val Leu
                260                 265                 270

Pro Gly Glu His Asn Leu Glu Asn Ile Leu Ala Ala Val Leu Ala Cys
            275                 280                 285

Ile Leu Ala Gly Val Pro Ile Lys Ala Ile Ile Asp Ser Leu Thr Thr
290                 295                 300

Phe Ser Gly Ile Glu His Arg Leu Gln Tyr Val Gly Thr Asn Arg Thr
305                 310                 315                 320

Asn Lys Tyr Tyr Asn Asp Ser Lys Ala Thr Asn Thr Leu Ala Thr Gln
                325                 330                 335

Phe Ala Leu Asn Ser Phe Asn Gln Pro Ile Ile Trp Leu Cys Gly Gly
            340                 345                 350

Leu Asp Arg Gly Asn Glu Phe Asp Glu Leu Ile Pro Tyr Met Glu Asn
                355                 360                 365

Val Arg Ala Met Val Val Phe Gly Gln Thr Lys Ala Lys Phe Ala Lys

-continued

```
              370                 375                 380
Leu Gly Asn Ser Gln Gly Lys Ser Val Ile Glu Ala Asn Asn Val Glu
385                 390                 395                 400

Asp Ala Val Asp Lys Val Gln Asp Ile Ile Glu Pro Asn Asp Val Val
                405                 410                 415

Leu Leu Ser Pro Ala Cys Ala Ser Trp Asp Gln Tyr Ser Thr Phe Glu
                420                 425                 430

Glu Arg Gly Glu Lys Phe Ile Glu Arg Phe Arg Ala His Leu Pro Ser
            435                 440                 445

Tyr
```